(12) United States Patent
Ladebeck

(10) Patent No.: US 8,338,794 B2
(45) Date of Patent: Dec. 25, 2012

(54) DETECTION DEVICE

(75) Inventor: Ralf Ladebeck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 714 days.

(21) Appl. No.: 12/458,367

(22) Filed: Jul. 9, 2009

(65) Prior Publication Data

US 2010/0006782 A1 Jan. 14, 2010

(30) Foreign Application Priority Data

Jul. 10, 2008 (DE) .......................... 10 2008 032 480

(51) Int. Cl.
*G01T 1/24* (2006.01)
(52) U.S. Cl. .............................. 250/370.15; 250/370.11
(58) Field of Classification Search ............. 250/370.11, 250/370.15
See application file for complete search history.

(56) References Cited

U.S. PATENT DOCUMENTS

| | | | |
|---|---|---|---|
| 2,251,708 A * | 8/1941 | Hefele ........................... | 342/433 |
| 4,631,636 A * | 12/1986 | Andrews ........................ | 361/699 |
| 6,011,313 A * | 1/2000 | Shangguan et al. .......... | 257/778 |
| 6,596,131 B1* | 7/2003 | Scott et al. ............... | 204/192.12 |
| 7,218,112 B2 | 5/2007 | Ladebeck et al. | |
| 2003/0117787 A1* | 6/2003 | Nakauchi ...................... | 361/818 |
| 2005/0111612 A1* | 5/2005 | Ikhlef et al. ..................... | 378/19 |
| 2005/0113667 A1* | 5/2005 | Schlyer et al. ............... | 600/411 |
| 2007/0102641 A1 | 5/2007 | Corbeil et al. | |
| 2007/0267577 A1* | 11/2007 | Kindem ................... | 250/370.15 |

FOREIGN PATENT DOCUMENTS

EP 1642530 A1 4/2006

* cited by examiner

*Primary Examiner* — David Porta
*Assistant Examiner* — Shun Lee
(74) *Attorney, Agent, or Firm* — Harness, Dickey & Pierce, P.L.C.

(57) ABSTRACT

A detection device with at least one detector and a processing unit for processing signals of the detector is disclosed. In at least one embodiment, the detection device includes at least one cooling unit for cooling the detector and the processing unit. A shielding is provided for the detector and the processing unit. The shielding includes at least two linked sections, of which a first section has a higher electrical conductivity than a second section, the second section being in thermal contact with the cooling unit.

17 Claims, 3 Drawing Sheets

DETECTION DEVICE

PRIORITY STATEMENT

The present application hereby claims priority under 35 U.S.C. §119 on German patent application number DE 10 2008 032 480.9 filed Jul. 10, 2008, the entire contents of which are hereby incorporated herein by reference.

FIELD

At least one embodiment of the present invention generally relates to a detection device with at least one detector and/or to a processing unit for processing signals of the detector, with at least one cooling unit being provided for cooling the detector and the processing unit.

BACKGROUND

In medical imaging so-called hybrid modalities, such as PET-CT, SPECT-CT, PET-MR and SPECT-MR for example, are becoming increasingly important. The meanings of these abbreviations are as follows:
PET: Positron Emission Tomography
CT: Computed Tomography
SPECT: Single Photon Emission Computed Tomography
MR: Magnet Resonance Tomography The advantage of these combinations is the connection of a modality with a high local resolution (especially MR or CT) with a modality with high sensitivity (especially SPECT or PET). The description below refers to a combined PET-MR system. Embodiments of the present invention can however be generally transferred to all forms of hybrid modalities or to measurement methods associated therewith.

PET uses the particular properties of positron emitters and positron annihilation in order to determine quantitatively the function of organs or cell areas. In such cases the appropriate radio pharmaceuticals which are marked with radio nuclides are administered to the patient. As they decay, the radio nuclides emit positrons which after a short distance interact with an electron, which causes what is referred to as an annihilation to occur. During this process two Gamma quanta occur which fly off in opposite directions (displaced by 180°). The Gamma quanta are detected by two opposite PET detector modules within a specific time window (coincidence measurement), by which the location of the annihilation is determined to a position on the connecting line between these two detector modules.

For verification the detector module must generally cover a large part of the gantry arc length for PET. It is divided up into detector elements with sides of a few millimeters in length in each case. On detection of a Gamma quantum each detector element generates an event recording which specifies the time as a well as the verification location, i.e. the corresponding detector element. This information is transferred to a fast logic and compared. If two events coincide in a maximum time interval then it is assumed that a Gamma decay process is occurring on the connecting line between the two corresponding detector elements. The PET image is reconstructed with a tomography algorithm, known as the back projection.

Since MR systems operate with high magnetic fields, the use of materials within these systems which are compatible with said fields is necessary. Attention should be paid in particular in the construction of PET detectors in combined PET-MR systems to the insensitivity of the detectors to magnetic fields.

In US 2007/0102641 A1 a combined PET-MR system is described in which lutetium oxyorthosilicate (LSO) is used as scintillation crystal for converting the Gamma quanta into light and Avalanche Photo Diodes (APD) are used for detection of the light. The APDs are connected with pre-amplifiers. A ring of such PET detectors is arranged within an MR device. This allows MR and PET data sets to be recorded simultaneously. A comparable arrangement is known from U.S. Pat. No. 7,218,112 B2.

With the frequently used semiconductor amplifiers and semiconductor detectors (Avalanche Photo Diodes, APD) in particular the amplification is dependent on the temperature. Since the components are subjected to temperature variations during operation, a cooling is necessary. Feeding in cooled air allows the temperature of the amplifier and photodiodes to be regulated. When air at a constant temperature is used the temperature of the amplifier is a result of the equilibrium of the generated heat and the heat emitted through the air over the surfaces of the amplifier. The cooling can be used in the same way for other parts of the detection system.

The APDs are however not only subjected to temperature fluctuations because of their operation. In particular the proximity to the gradient coil and the excitation coil of the MR system caused by the compact design represents a heat source acting from outside on the APD. The temperature of a gradient coil is typically between 20 and 80° C. during operation. These temperature differences also affect the APDs and thereby their amplification. The effects of this heat source can only be overcome with difficulty using air cooling. It is therefore of advantage to provide water cooling.

In addition to the problem of cooling, PET detectors in particular are very sensitive to faults caused by electromagnetic fields. The very small currents measured with time resolution are typically responsible for these faults. Integration into the MR system then subjects the PET detector to the fields which are necessary for imaging by way of MR. Gradient fields which are driven by an amplifier operating in accordance with the switched-mode converter principle cause faults in such cases of frequencies ranging up to a few 100 kHz. The APD is to be shielded from these faults. In addition the HF system of the MR device can generate higher frequencies which are also be taken into consideration.

It is known that electro magnetically-sensitive components can be shielded by copper foil against electromagnetic faults for example. The shielding effect is produced by currents being induced in the shielding material, which then cancel out the electromagnetic fields inside the shielding. The thickness and the geometry of the shielding structure define the frequency range in which the shielding is effective.

It is thus possible to provide a PET detector block with a shielding envelope. Since however the heating of the shielding caused by the switching of the gradients increases in proportion to the surface, it is desirable to embody the shielding small if possible in order not to introduce any unnecessary heat into the PET detection system.

In at least one embodiment of the present invention, an improved detection device with optimized shielding is provided.

In accordance with one version of at least one embodiment of the invention, a detection device with at least one detector and a processing unit for processing signals of the detector is specified, with at least one cooling unit for cooling the detector and processing unit being provided. Electromagnetic shielding is provided for the detector and the processing unit which comprises that least two electrically-connected sections of which are first section has a higher electrical conductivity than a second section and with the second section being in thermal contact with the cooling unit. The detector and the processing unit for the signals of the detector can be efficiently cooled by the cooling unit provided.

The fact that the shielding comprises two sections with different levels of electrical conductivity means that the power dissipation produced by the shielding falls primarily on the section with the low electrical conductivity. However this section is in contact with the cooling unit so that the heat arising is able to be removed efficiently. Both the detector and also the processing unit are consequently not affected by the heating up of the shielding so that the shielding can be arranged very close to the processing unit and the detector. This means that the shielding is able to be made a significantly smaller by comparison with a complete encapsulation of the PET detector block.

A different electrical conductivity means that the electrical resistance (e.g. per unit of surface) of the shielding is different in different sections. A low electrical conductivity means in such cases that the electrical resistance is increased by comparison with the section with the higher electrical conductivity.

In an advantageous embodiment of the invention the shielding only partly surrounds the detector and the processing unit. This typically makes the detector accessible for optical signals. It should be ensured that the cutout areas of the shielding do not adversely affect its shielding effect in the relevant frequency range.

In an advantageous embodiment of the invention, the detector comprises a light generator and a light sensor, with the light sensor being arranged such that it converts light of the light generator into an electrical signal and can transmit it to the processing unit. For example Gamma quanta can be converted by the light generator into visible light and then by way of the light sensor into an electrical signal by way of such a detector.

One embodiment of the invention is advantageous in that the first section of the shielding is arranged between the light generator and the light sensor and features at least one cutout which is arranged such that the light of the light generator can reach the light sensor. The cutout makes it possible for light from the light generator to get through the shielding to the light sensor.

In an advantageous embodiment of the invention the first section of the shielding features an interruption assigned to the cutout which is embodied such that a current path surrounding the cutout is electrically interrupted. This effectively prevents in the case of incident electromagnetic radiation around the cutout eddy currents being generated which generate a heating-up in the non-cooled area of the shielding.

BRIEF DESCRIPTION OF THE DRAWINGS

Further advantages and embodiments of the invention emerge from the example embodiments described below in conjunction with key figures. The figures show.

DETAILED DESCRIPTION OF THE EXAMPLE EMBODIMENTS

Figure 1:
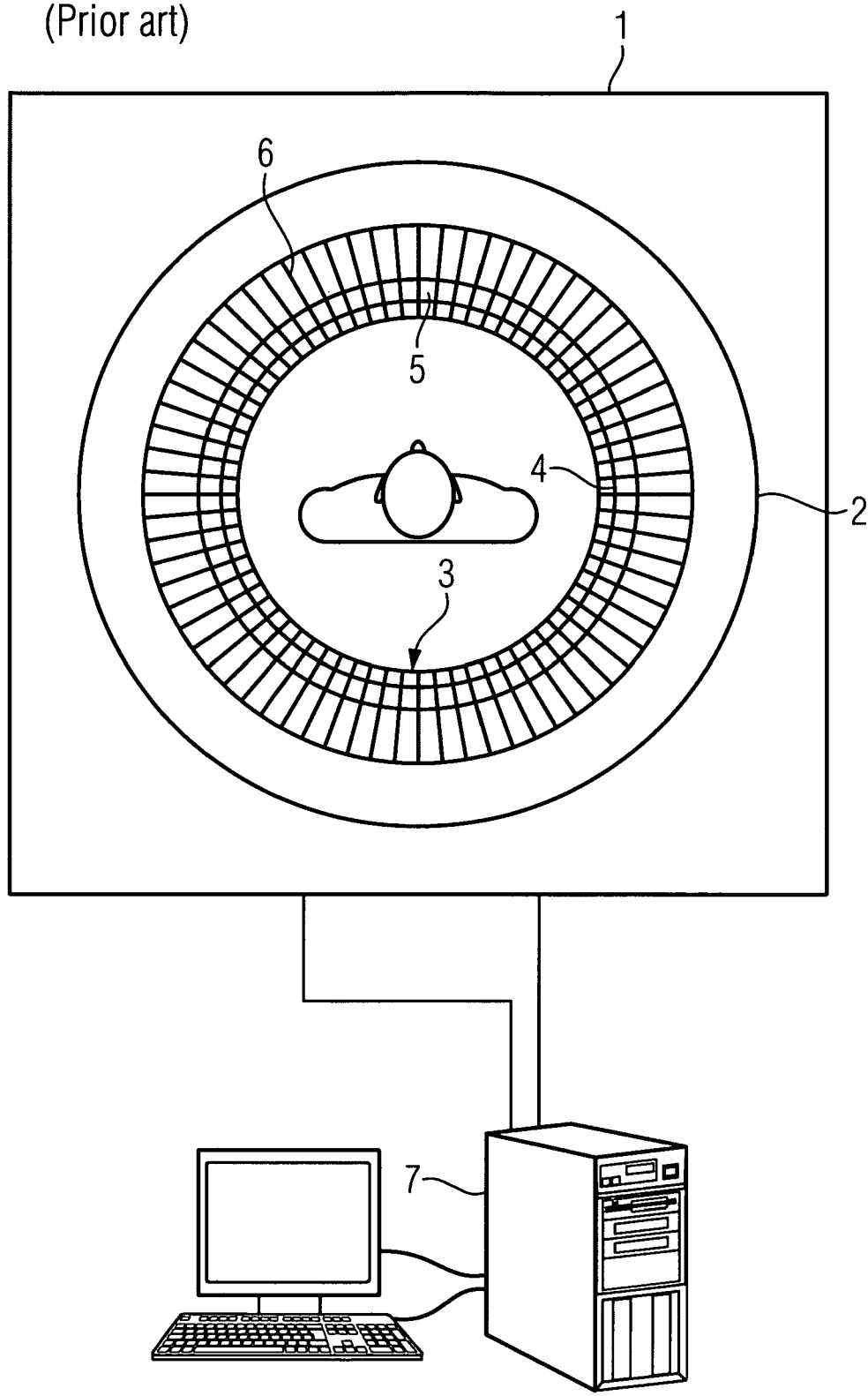
FIG. 1 a schematic diagram of a PET-MR combination device.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention may preferably be used with a combined PET-MR device. A combined device has the advantage that both MR and also PET data can be obtained isocentrically. This makes it possible to precisely define the examination volume within the region of interest with the data of the first modality (PET) and to use this information in the further modality (e.g. magnetic resonance). A transmission of the volume information of the region of interest from an external PET to an MR device is possible, but this involves greater outlay for the registration of the data. In general all data able to be determined by magnetic resonance or by other imaging methods can be determined on the region of interest selected on the PET data set. For example, instead of the spectroscopy data, fMRI data, diffusion data, T1 or T2-weighted images or quantitative parameters can be obtained by way of magnetic resonance examinations in the region of interest. Likewise methods of computer tomography (e.g. perfusion measurement, multiple energy imaging) or x-rays can be used.

In addition however it is also possible, by using a number of so-called tracers, to represent various biological characteristics in the PET data set and thus to optimize the region of interest and the volume defined thereby even further or to select a number of different examination volumes at once which are then analyzed in subsequent examinations.

In a similar way, the example embodiments of the invention can also be applied to hybrid modalities with a non-isocentric examination volumes, such as known PET-CT systems for example.

FIG. 1 shows a known facility for overlaid MR and PET image display. The facility 1 consists of a known MR tube 2. The MR tube 2 defines a longitudinal direction z which extends orthogonally to the plane of the drawing of FIG. 1.

As it shown in FIG. 1, a number of PET detection units 3 are arranged coaxially within the MRI tubes 2 around the longitudinal direction z in pairs opposite one another. The PET detection units 3 preferably consist of an APD photodiode array 5 with an upstream array of LSO crystals 4 and an electrical amplifier circuit (AMP) 6. However the invention is not restricted to the PET detection units 3 with the APD photodiode array 5 and the upstream array of LSO crystals 4, but instead other types of photodiodes, crystals and apparatus can equally well be used for detection.

The image processing for overlaid MR and PET image presentation is undertaken by a computer 7.

Along its longitudinal direction the MR tube 2 defines a cylindrical, first image field. The plurality of the PET detection units 3 defines a cylindrical second image field along the longitudinal direction z. Inventively the second image field of the PET detection units 3 essentially coincides with the first image field of the MR tubes 2. This is implemented by an appropriate adaptation of the arrangement density of the PET detection units 3 along the longitudinal direction z.

Figure 2:
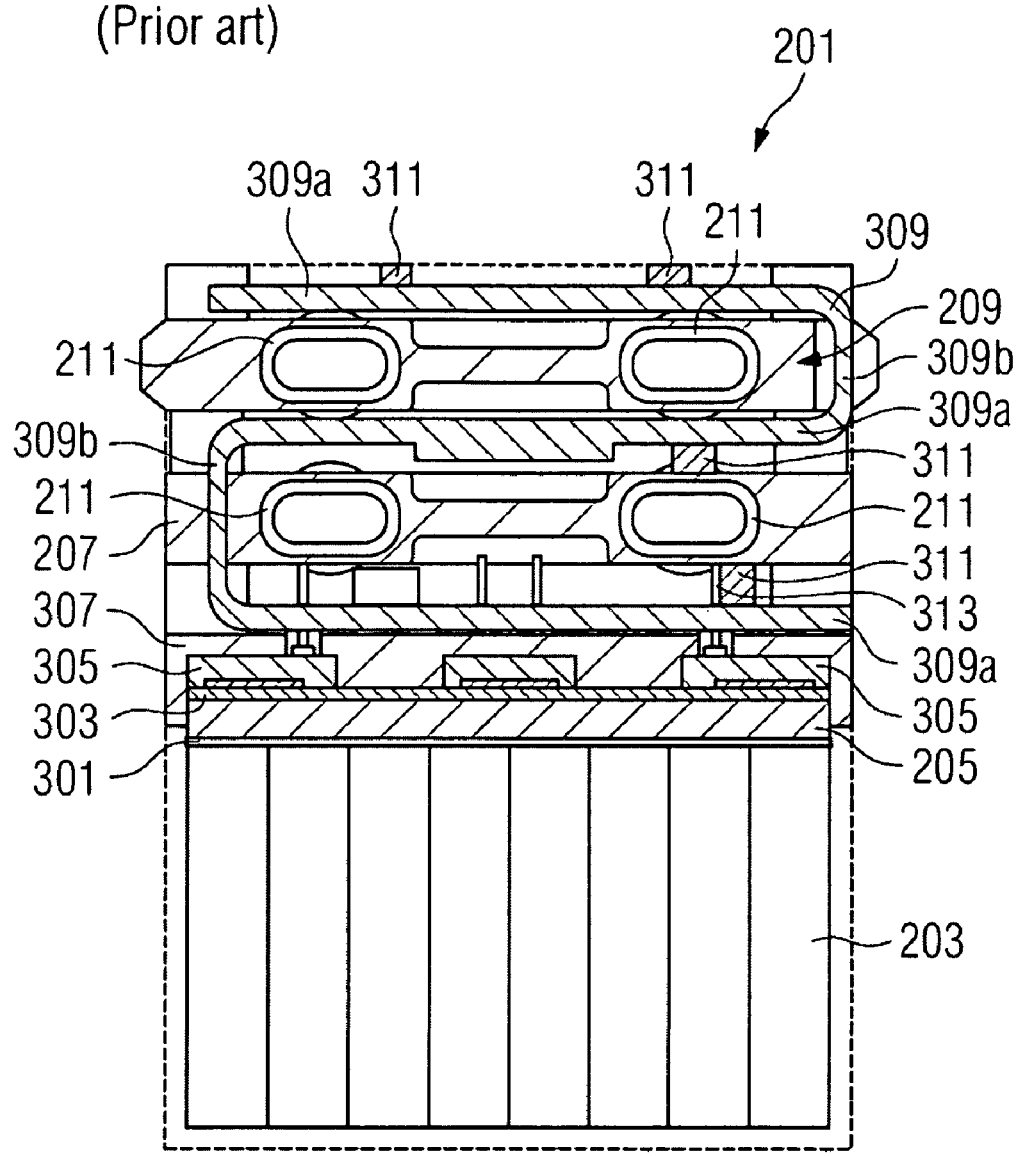
FIG. 2 a schematic diagram of a PET detector block.

FIG. 2 shows a schematic sectional image through a detection unit 201. An interface layer 301 is inserted between an LSO crystal 203 and an optical waveguide 205. Applied to the optical waveguide 205 is an intermediate layer 303 above which a number of APDs are arranged within a holder 307. The two cooling units 207 and 209 are in turn arranged above the holder 307. The cooling line 211 through which cooling water can be applied to the cooling units 207 and 209 runs twice in each case within the cooling units 207 and 209. The cooling line 211 is embodied within the cooling units 207 and 209 such that coolant coming from a coolant source not shown in the figure initially flows through the cooling unit 207. In the further course of the cooling line 211 this routes the coolant through the cooling units 209, in this way both the cooling unit 207 and also the cooling units 209 can be used to cool the APD 305 by way of a single coolant source.

A circuit board 309 is inserted between the cooling units 207 and 209 as well as the holder 307. This features rigid sections 309a and flexible sections 309b and can thus be produced in one piece. The circuit board 309 is equipped with various electronic components 311. It also features electrical connections 313 to the APD 305. The components 311 located on the different rigid sections 309a can be connected via conductor tracks across the flexible sections. The connection of the rigid and flexible sections 309a and 309b still allows the compact design shown to be realized with a comparatively large circuit board surface.

The electronic components 311 or the circuit board 309 are in thermal contact with the cooling units 207 and 209 in a number of places. Consequently these are cooled by the cooling units 207 and 209. Since a part of the circuit board 309 and a few of the components 313 located on it lie between the cooling units 207 and the holder 307 of the APD 305, there is no provision in this version for a direct thermal contact between the APD 305 and the cooling unit 207. The thermal conductivity from the APD 305 via the holder 307, the circuit board 309 and the components 313 to the cooling unit 207 is however sufficiently high with the correct choice of the materials used to guarantee a good thermal coupling of the APD 305 to the cooling unit 207.

Gamma quanta generated by PET events are converted into light by scintillation by the LSO crystal 203. The generated light is forwarded by the optical waveguide 205 to the APDs 305. These generate pulses from the incident flow of light which are passed on via the lines 313 to the circuit board 309 and its components 311. Provisional processing of the received signals is undertaken on the circuit board 309. The amplification of the APDs is temperature-dependent, which would lead to measurement inaccuracies with insufficient cooling. Thus a temperature stabilization in the range of a few degrees Celsius is to be realized here in order to guarantee the smooth operation of the detection unit. The cooling unit 207 is in good thermal contact with the holder 307 of the APDs 305 such that an efficient and simple-to-realize cooling of the APDs 305 is provided. The inherent heating up of the APDs 305 during operation can be compensated for in this way.

The compact design of PET-MR systems means that generally several of the detection units 201 are close to diverse sources of heat once the unit is assembled. In such cases the gradient coil in particular plays a significant part. Depending on operating state, its temperature fluctuates between around 20 and 80° C. The external incident heat resulting from this onto the APDs 305 has a significant influence on their operating temperature and thus on their amplification. This incident heat is greatly reduced by the cooling unit 209 lying between the gradient coil and the APDs 305 so that the operating behavior of the APDs 305 is no longer subjected to any negative influences.

Figure 3:
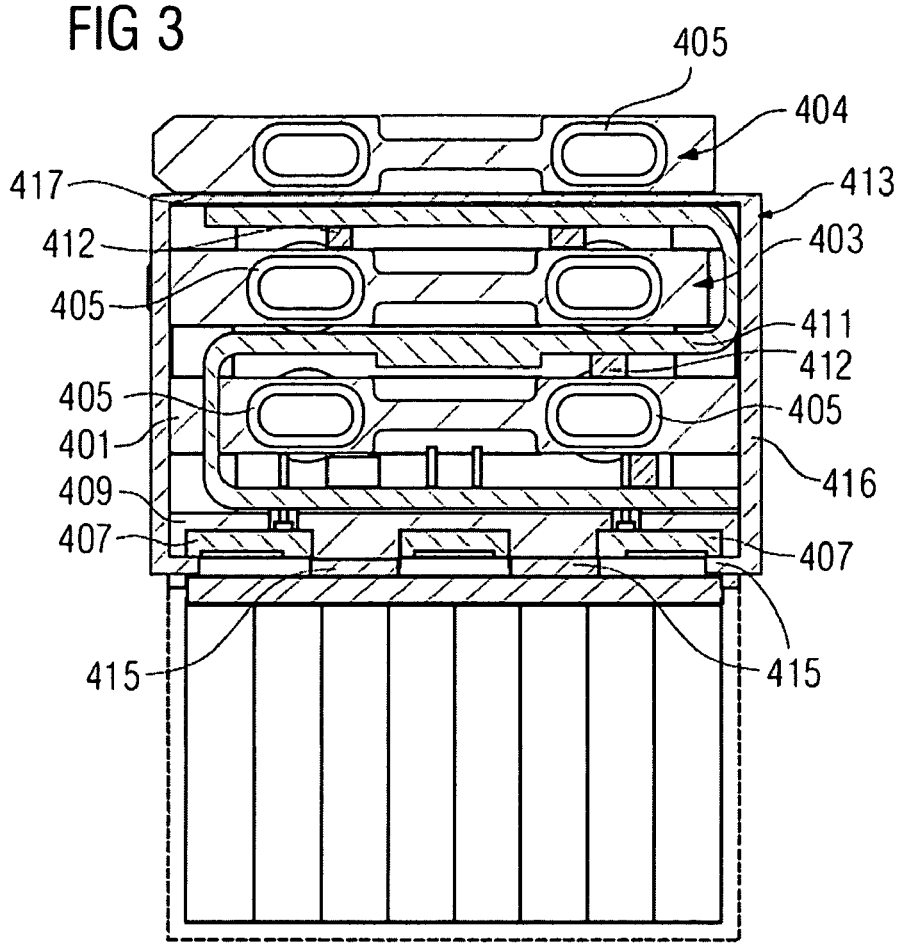
FIG. 3 a schematic diagram of an example embodiment of the invention.

FIG. 3 shows a schematic diagram of a detection unit similar to that shown in FIG. 2. The diagram shows three cooling units 401, 403 and 404 through which cooling lines 405 pass. Three APDs 407 are connected by way of a holder 409 to a processing unit 411 for signals of the APDs 407. The processing unit 411 comprises electronic components 412 and is in direct thermal contact with the cooling units 401 and 403. The processing unit 411 and the APDs 407 as well as the holder 409 are surrounded by a shielding 413. The shielding 413 is not shown true-to-scale in this diagram. It consists of a copper foil and comprises a number of sections 415, 416 and 417, parts of which have different thicknesses. The section 415 in the shielding 413 is interrupted in several places so that light can enter from below into the APDs 407.

The section 417 of the shielding is in direct thermal contact with the processing unit 411 and with the cooling unit 404, so that heat arising in it is able to be efficiently removed via the cooling unit 404. The different thicknesses of the sections 415, 416 and 417 of the shielding means that the heat generated with incident HF radiation arises primarily in section 417 so that heating barely occurs in the vicinity of the sensitive APDs 407. The shielding typically consists in the area of the sections 415 and 416 of a copper foil 100 μm thick, in section 417 on the other hand of a copper foil 17 μm thick. However other materials or structures can be provided for shielding.

Figure 4:
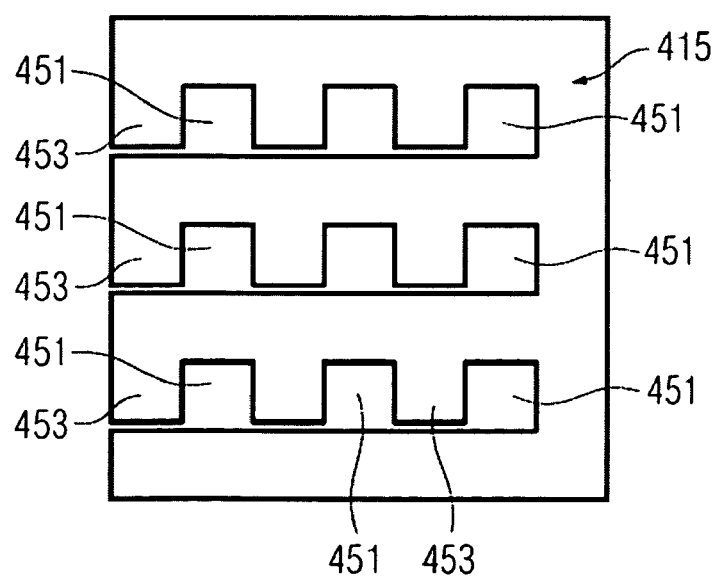
FIG. 4 a schematic view of shielding for a detector array.

FIG. 4 shows the section 415 of the shielding 413 in a front view. The section 415 has cutouts through which light can fall on to the APDs lying below them. In addition each cutout 451 is assigned an interruption 453. The shielding 413 is electrically interrupted at each interruption 453, so that no eddy currents can be formed under the influence of electromagnetic radiation around the cutout in 451 which would generate heat.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What I claimed is:

1. A detection device comprising:
   at least one detector; and
   a processing unit to process signals of the at least one detector;
   at least one cooling unit to cool the at least one detector and the processing unit;
   a shielding for the at least one detector and the processing unit, the shielding including at least two electrically connected sections, a first section of the at least two electrically connected sections including a relatively higher electrical conductivity than a second section of the at least two electrically connected sections, the second section being in thermal contact with the at least one cooling unit and the first section and the second section are composed of the same material.

2. The detection device as claimed in claim 1, wherein electrical conductivities of the first and second sections of the shielding are selected such that, for incident electromagnetic radiation, significantly lower heat loss is generated in the first section than in the second section.

3. The detection device as claimed in claim 2, further comprising a plurality of light generators and light sensors assigned to each other, arranged in rows and columns respectively, wherein the first section of the shielding features a cutout between each of the light generators and the respective light sensor assigned to thereto.

4. The detection device as claimed in claim 2, wherein the processing unit includes at least one circuit board on which the electronic components are arranged and which is arranged such that each of the components is in thermal contact with one of the at least one cooling unit.

5. The detection device as claimed in claim 1, wherein the shielding only partly surrounds the at least one detector and the processing unit.

6. The detection device as claimed in claim 1, wherein the at least one detector includes a light generator and a light sensor, with the light sensor being arranged to convert light of the light generator into an electrical signal and to transfer the electrical signal to the processing unit.

7. The detection device as claimed in claim 6, wherein the first section of the shielding is arranged between the light generator and the light sensor, the first section including at least one cutout, arranged such that the light of the light generator can reach the light sensor.

8. The detection device as claimed in claim 7, wherein the first section of the shielding includes an interruption assigned to the cutout, embodied such that a current path surrounding the cutout is interrupted.

9. The detection device as claimed in claim 6, wherein the light sensor is embodied as an avalanche photodiode (APD).

10. The detection device as claimed in claim 9, wherein the APD is arranged to be in thermal contact with the at least one cooling unit.

11. The detection device as claimed in claim 6, wherein the light generator is embodied as a scintillation crystal.

12. The detection device as claimed in claim 1, further comprising a plurality of light generators and light sensors assigned to each other, arranged in rows and columns respectively, wherein the first section of the shielding features a cutout between each of the light generators and the respective light sensor assigned to thereto.

13. The detection device as claimed in claim 1, wherein the processing unit includes at least one circuit board on which the electronic components are arranged and which is arranged such that each of the components is in thermal contact with one of the at least one cooling unit.

14. The detection device as claimed in claim 13, wherein the at least one circuit board is arranged alternating with the at least one cooling unit.

15. The detection device as claimed in claim 1, wherein the at least one detector is embodied as a Positron Emission Tomography (PET) detector.

16. The detection device as claimed in claim 1, wherein a thickness of the first section is different than a thickness of the second section so that the first section includes the relatively higher electrical conductivity than the second section.

17. The detection device as claimed in claim 1, wherein the second section is in direct thermal contact with the at least one cooling unit.

* * * * *